US006379387B1

(12) United States Patent
Tornier

(10) Patent No.: US 6,379,387 B1
(45) Date of Patent: Apr. 30, 2002

(54) ELBOW PROSTHESIS

(75) Inventor: Alain Tornier, Saint Ismier (FR)

(73) Assignee: Tornier SA, Saint-Ismier (FR)

( * ) Notice: Subject to any disclaimer, the term of this patent is extended or adjusted under 35 U.S.C. 154(b) by 0 days.

(21) Appl. No.: 09/568,421

(22) Filed: May 10, 2000

(30) Foreign Application Priority Data

May 14, 1999 (FR) ............................................ 99 06314

(51) Int. Cl.[7] ................................................ A61F 2/38
(52) U.S. Cl. .................................. 623/20.12; 623/20.13
(58) Field of Search ........................... 623/20.11, 20.12, 623/20.13

(56) References Cited

U.S. PATENT DOCUMENTS

| 4,131,956 A | * | 1/1979 | Treace ..................... 623/20.11 |
| 4,242,758 A | | 1/1981 | Amis et al. |
| 4,383,337 A | | 5/1983 | Volz et al. |
| 4,538,306 A | | 9/1985 | Dorre et al. |
| 4,822,364 A | | 4/1989 | Inglis et al. |
| 5,133,761 A | | 7/1992 | Krouskop |
| 5,314,484 A | * | 5/1994 | Huene ..................... 623/20.12 |
| 5,702,471 A | | 12/1997 | Grundei et al. |
| 5,723,015 A | * | 3/1998 | Risung et al. ........... 623/20.12 |

FOREIGN PATENT DOCUMENTS

| DE | 9512854 | 8/1996 |
| EP | 0006314 | 1/1980 |
| EP | 0098466 | 1/1984 |
| EP | 0913133 | 5/1999 |
| FR | 2663838 | 1/1992 |
| GB | 1537479 | 12/1978 |

* cited by examiner

Primary Examiner—David J. Isabella
(74) Attorney, Agent, or Firm—Dowell & Dowell, P.C.

(57) ABSTRACT

This invention relates to an elbow prosthesis comprising a humeral component forming a first, substantially cylindrical articulating surface and an ulnar component forming a second articulating surface adapted to be arranged around a part of this first articulating surface and to pivot about a longitudinal axis of this first articulating surface. The ulnar component is provided with the means for mounting a locking element forming a third articulating surface, extending the second articulating surface and adapted to be disposed around the first articulating surface, these second and third articulating surfaces extending together, in transverse section, over more than 180° about the first articulating surface.

15 Claims, 7 Drawing Sheets

ELBOW PROSTHESIS

BACKGROUND OF THE INVENTION

1. Field of the Invention

The present invention relates to an elbow prosthesis comprising at least one humeral component and one ulnar component.

2. Description of the Related Art

As a function of the articular clearance and of the mode of coupling the humeral and ulnar prosthetic elements together, two principal types of prostheses are distinguished:

prostheses with hinge arrangements, in which a common hinge pin is introduced in aligned orifices provided on the humeral component and on the femoral component. Taking into account the mode of assembling these prostheses the, the hinge pin which defines the articulating surface necessarily presents a rectilinear generatrix, which is substantially different from the natural articulating surface of the trochlea. These hinge arrangements present good stability and allow a rotation in the sagittal plane of the joint. However, they prevent transverse movements such as the varus-valgus movement or a movement of ulnar axial rotation. To allow such a movement, the hinge must be provided with a considerable radial clearance, which leads to premature wear of the articulating surfaces.

sliding prostheses, as known in particular from U.S. Pat. No. 4,242,758, in which the ulnar component cothemtheotheies into abutment on a substantially cylindrical humeral articulating surface. Such prostheses allow transverse movements, but are unstable perpendicularly and/or parallel to the sagittal plane, hence there is a considerable risk of dislocation or transverse instability inducing parasitic movements when the elbow is flexed.

It is a particular object of the present invention to overcome these drawbacks by proposing an elbow prosthesis which allows certain transverse movements, such as the varus-valgus movement, while presenting a largely increased stability over known sliding prostheses.

SUMMARY OF THE INVENTION

To that end, the invention relates to an elbow prosthesis comprising a humeral component forming a first, substantially cylindrical articulating surface and an ulnar component forming a second articulating surface adapted to be arranged around a part of this first articulating surface and to pivot about a longitudinal axis of this first articulating surface, characterized in that the ulnar component is provided with means for mounting a locking element forming a third articulating surface, extending the second articulating surface and adapted to be disposed around the first articulating surface, these second and third articulating surfaces extending together, in transverse section of the first articulating surface, over more than 180° about the first articulating surface.

Thanks to the invention, the second and third surfaces of the ulnar component and of the locking element make it possible to surround or to enclose the first articulating surface, this eliminating the risks of dislocation of the joint. The geometry of the articulating surfaces may be chosen to be close to the natural articulating surfaces and, in particular, is not limited to the cylindrical surfaces with rectilinear generatrix used up to the present time in hinge-type prostheses. In effect, the cylindrical nature of the first articulating surface means that it is generated by rotation of a generatrix about an axis, its generatrix not necessarily being rectilinear but may be concave, which makes it possible to approach the natural morphology of the trochlea best.

According to advantageous aspects of the invention, the prosthesis incorporates one or more of the following features:

The second and third articulating surfaces extend together over an angle included between 190° and 360°, preferably between 225° and 315°, preferably still of the order of 270°, about the first articulating surface.

The prosthesis comprises means for adjusting, as a function of the patient's morphology, the position of the longitudinal axis of the first surface with respect to the longitudinal axis of an anchoring rod of the humeral component. In effect, the trochlea may be more or less forward in the sagittal plane with respect to the longitudinal axis of the humerus, independently of the size of the bone, this morphological variation not, up to the present time, being taken into account by elbow prostheses. The prosthesis of the present invention therefore makes it possible to take this variable into account when placing a prosthesis. In particular, the first surface may be provided to be formed by an elongated piece while tabs fast with the anchoring rod are provided with bores for receiving an assembly pin, the relative position of the bores of the piece and of the tabs being adapted as a function of the patient's morphology. For example, the prosthesis may comprise a plurality of elongated pieces and/or a plurality of rods, these pieces and rods being adapted to be assembled together and allowing different positions of the longitudinal axis of the substantially cylindrical parts with respect to the axes of the rods, to be obtained. According to another variant embodiment, the rod and the elongated piece forming the first surface may be provided to be fixed with respect to each other, in particular in one piece, the prosthesis comprising a plurality of such piece/rod assemblies of different geometries therefor a given size of humerus. It is then possible for the surgeon, when placing a prosthesis, to choose a rod/piece assembly as a function of the patient's morphology.

The ulnar element and the locking element are each provided with a free edge, the distance between these free edges being smaller than the minimum diameter of the first articulating surface when the locking element is mounted on the ulnar component. In this way, the assembly formed by the ulnar component and the locking element cannot be dislocated with respect to the first articulating surface.

The assembly means comprise at least one tapping for receiving a screw engaged in a housing provided in the locking element or a housing for receiving a screw adapted to be screwed in a corresponding tapping in the locking element.

The first articulating surface has a concave generatrix, while the second and third articulating surfaces present, in a plane of section parallel to the axis of the first articulating surface, a convex generatrix. Thanks to this arrangement, the axis of the varus-valgus movement is permanently located in the ulnar component, which gives a better transverse stability to the prosthesis thus produced, in particular with respect to the one known by U.S. Pat. No. 4,242,758, in which the axis of the varus-valgus movement is, in the extreme configurations, located in the bobbin forming the humeral element.

The first articulating surface extends in a fourth, substantially convex, articulating surface for bearing a radial component. This allows a total elbow prosthesis to be produced.

A functional clearance between the above-mentioned surfaces is formed by the difference of their diameters or radii of curvature of their respective generatrices.

The ulnar component and/or the locking element comprise a reinforcement and a lining mounted on the reinforcement by cooperation of shapes thanks to returns adapted to cover lateral fins of the reinforcement.

An orifice for passage of at least one suture thread is made near the longitudinal axis of the first articulating surface and parallel thereto.

BRIEF DESCRIPTION OF THE DRAWINGS

The invention will be more readily understood on reading the following description of two embodiments of an elbow prosthesis in accordance with its principle, given solely by way of example and made with reference to the accompanying drawings, in which.

DESCRIPTION OF PREFERRED EMBODIMENTS

Figure 1:
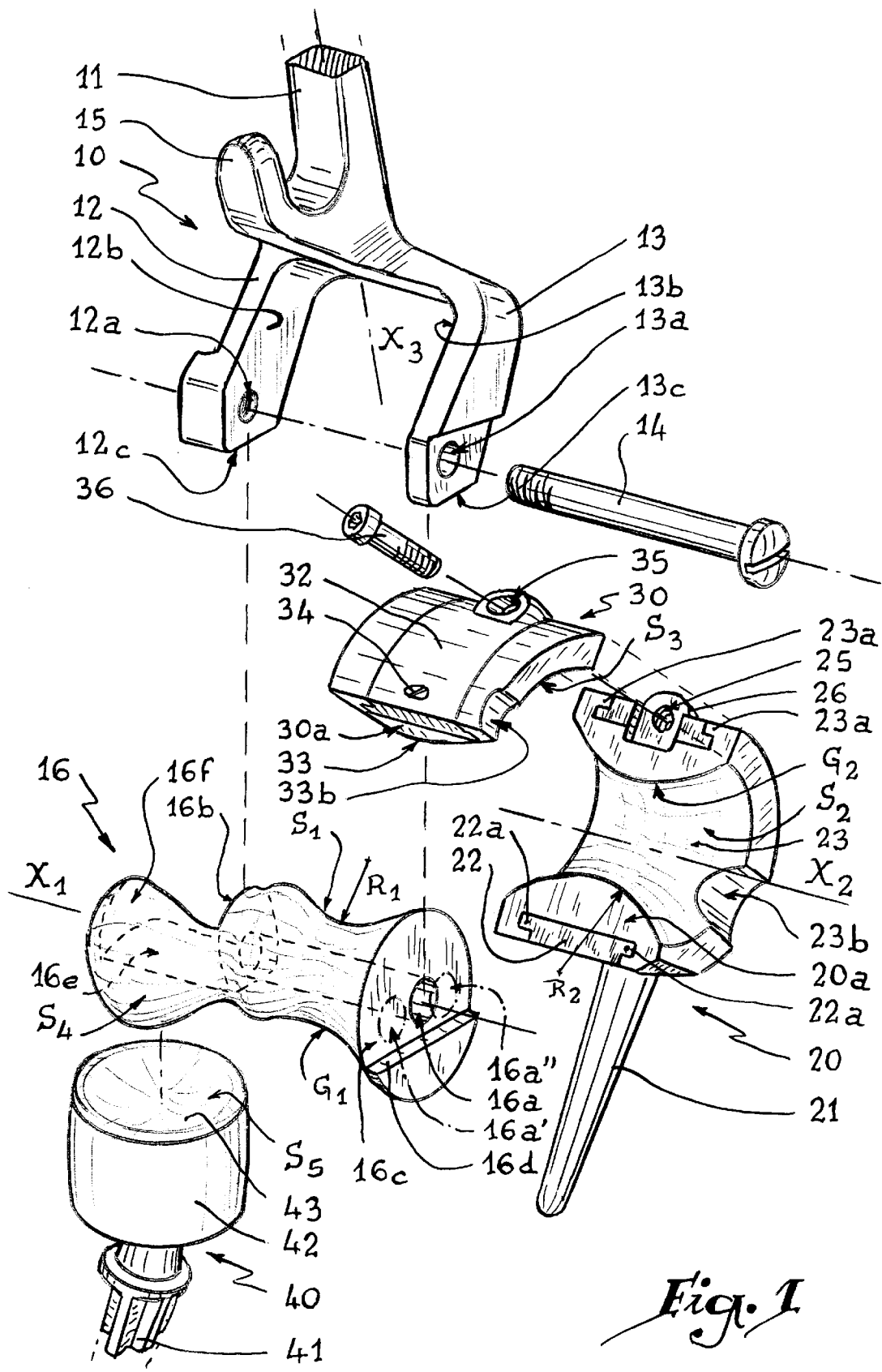
FIG. 1 is an exploded view in perspective of an elbow prosthesis according to the invention.

Referring now to the drawings, the prosthesis visible in FIGS. 1 to 6 comprises a humeral component 10 presenting a rod 11 intended to be driven in the medular channel of a humerus H and extending in two tabs 12 and 13 each pierced with an orifice 12a or 13a for passage of a screw 14 forming shaft. Orifice 12a is tapped, which enables it to cooperate with the outer threading of screw 14.

The rod 11 also extends in a third tab 15 intended to abut against the cortex of the humerus II and to prevent a possible forward tipping of the humeral rod.

An elongated body or piece 16 is provided with a central bore 16a whose dimensions allow it to receive the screw 14. Two end surfaces 16b and 16c of the piece 16 are provided to come respectively into contact with the opposite surfaces 12b and 13b of the tabs 12 and 13, while screw 14 traverses the orifices and bores 13a, 16a and 12a.

In this position shown in FIGS. 3 to 6, an end surface 13c of the tab 13 is in abutment against an end shoulder 16d of the piece 16. Similarly, an end surface 12c of the tab 12 comes into contact with a surface 16e of complementary shape provided on the piece 16, beyond the surface 16b. In this way, the piece 16 is immobilized in rotation about the screw 14 by cooperation of shapes of the surfaces 13c and 16d, on the one hand, 12c and 16e, on the other hand.

Figure 7:
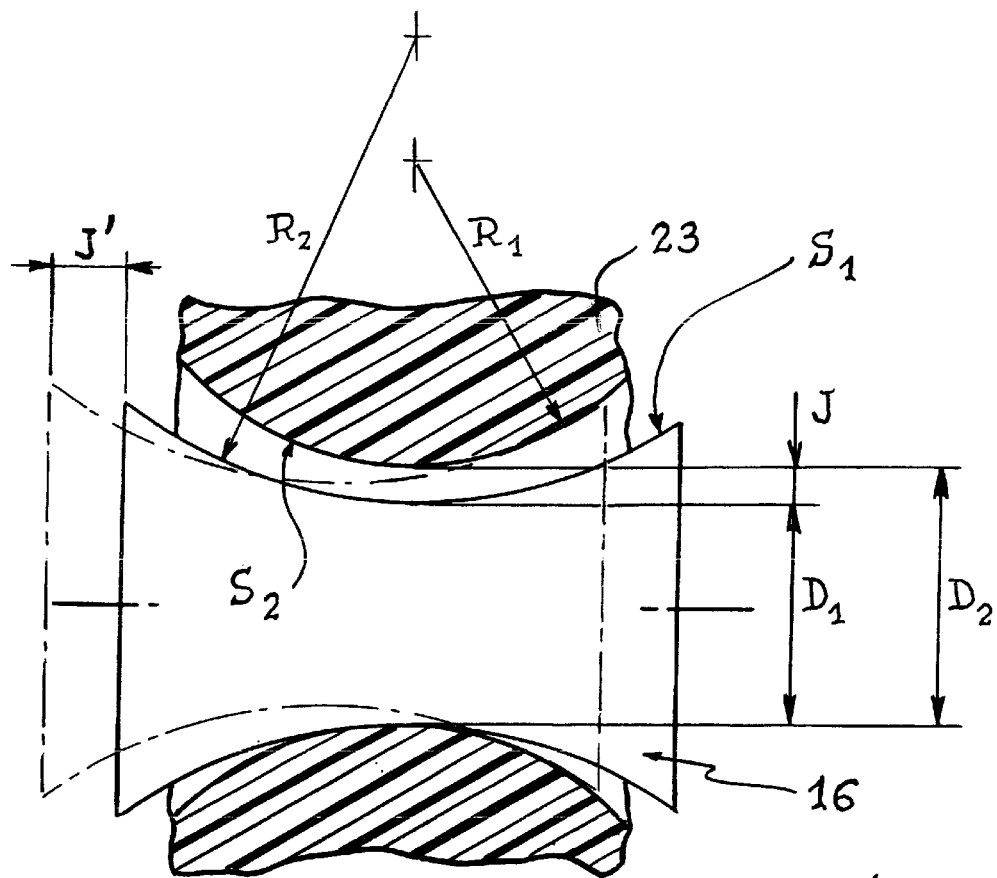
FIG. 7 schematically shows, on a larger scale and in longitudinal section, certain contact surfaces of the prosthesis of FIGS. 1 to 6.

Between the surfaces 16b and 16c, the piece 16 is substantially cylindrical and forms an articulating surface $S_1$ likewise substantially cylindrical, of which the generatrix $G_1$ is curved and concave, in that the diameter of the surface $S_1$ is minimum in the central part of that portion of the piece 16 included between the surfaces 16b and 16c. $X_1$ denotes the axis of symmetry of the surface $S_1$, $D_1$ its diameter, which is variable along axis $X_1$, and $R_1$ the radius of curvature of the generatrix $G_1$ in the plan of FIG. 7.

The piece 16 extends by an extension 16f of which the outer surface $S_4$ is convex. The extension 16f covers tab 12 when the piece 16 is mounted on tabs 12 and 13.

The whole of the humeral component 10 is made of metal.

An ulnar component 20 comprises a metal rod 21 intended to be inserted in the medullar channel of the ulna C and which extends in a likewise metallic tab 22 of concave shape of which the inner surface is coated with a lining 23 made of a material adapted for friction with the metallic piece 16, for example polyethylene. The lining 23 is mounted on the tab 22 by cooperation of shapes thanks to returns 23a which cover lateral fins 22a of the tab 22. A headless screw 24 makes it possible to immobilize elements 22 and 23 with respect to each other.

Figure 2:
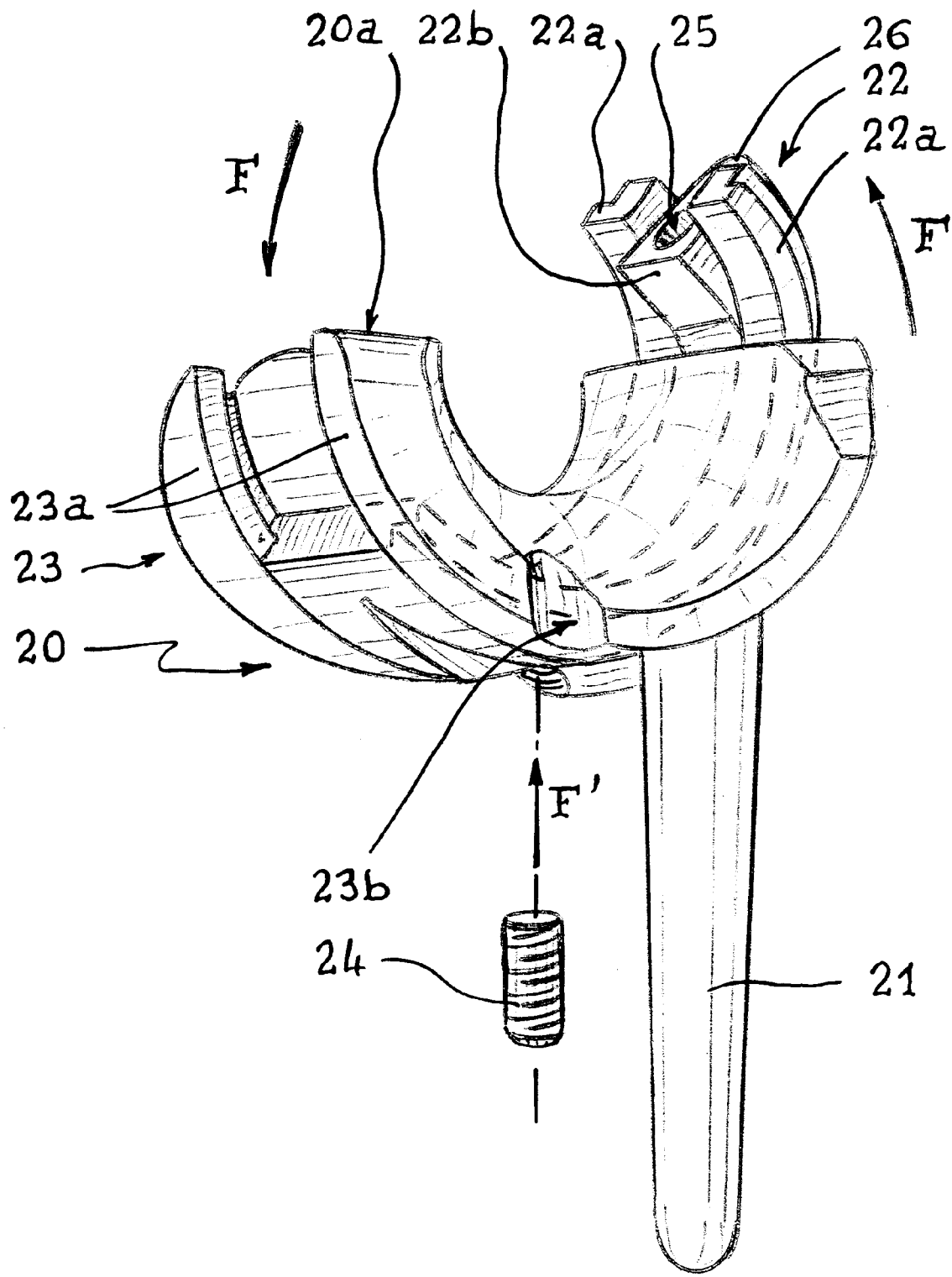
FIG. 2 is a view in perspective of the ulnar component of the prosthesis of FIG. 1 in the course of assembly.

The assembly of the lining 23 on the tab 22 is represented in FIG. 2. The lining 23 is engaged on the tab 22 so that its returns 23a cover the fins 22a and undergoes a movement of slide represented by arrows F until they come into abutment against a stop surface 22b formed on the interior of a boss 26 on the tab 22. When the lining 23 is in abutment against the surface 22b, the screw 24 is introduced and screwed in the lining 23 and in the tab 22, as represented by arrow F. The tab 22 then constitutes an enveloping reinforcement for the lining 23.

The process of assembly used between the lining 23, which may in particular be made of plastics material, and the tab 22, which is made of metal, presents the following advantages:

a considerable facility of machining of the lining 23, as its constituent material may be machined solely by turning, without resorting to numerical control machines.

a particularly efficient bold of the lining 23 on the tab 22.

the presence of a large quantity of matter, for example polyethylene, forming the lining 23 on either side of the metal forming the tab 22, which makes it possible to avoid any contact between the metal parts 16 and 22 during the articular movement.

Although the mode of assembly described hereinabove is particularly advantageous, the relative immobilization of the elements 22 and 23 may be effected by other means, in particular by blocking, crimping or clipping.

The lining 23 is provided with a lateral notch 23b in order not to interfere with the tissues passing near the component 20 when the prosthesis is in mounted position.

The inner surface of the lining 23 forms an articulating surface $S_2$ of shape complementary of that of surface $S_1$. $X_2$ denotes the central axis of the elements 22 and 23, $D_2$ the diameter of the surface $S_2$, this diameter being variable along axis $X_2$. In section in a plane parallel to axis $X_2$, the surface $S_2$ is convex, in that its generatrix $G_2$ is curved and convex, with a centre of curvature disposed towards the tab 22, i.e. the opposite of axis $X_2$. $R_2$ denotes the radius of curvature of the generatrix $G_2$.

The respective diameters $D_1$ and $D_2$ and the respective radii of curvature $R_1$ and $R_2$ of the surfaces $S_1$ and $S_2$ are substantially equal. The slight differences in values of $D_1$ and $D_2$, on the one hand, and of $R_1$ and $R_2$, on the other hand, make it possible to create a diametral functional clearance J and a longitudinal functional clearance J' which are exaggerated in FIG. 7 in order to render the drawing clearer. These functional clearances J and J' which have low values, allow the relative movement of varus-valgus and of axial rotation of the ulnar component 20 with respect to the humeral component 10.

Figure 3:
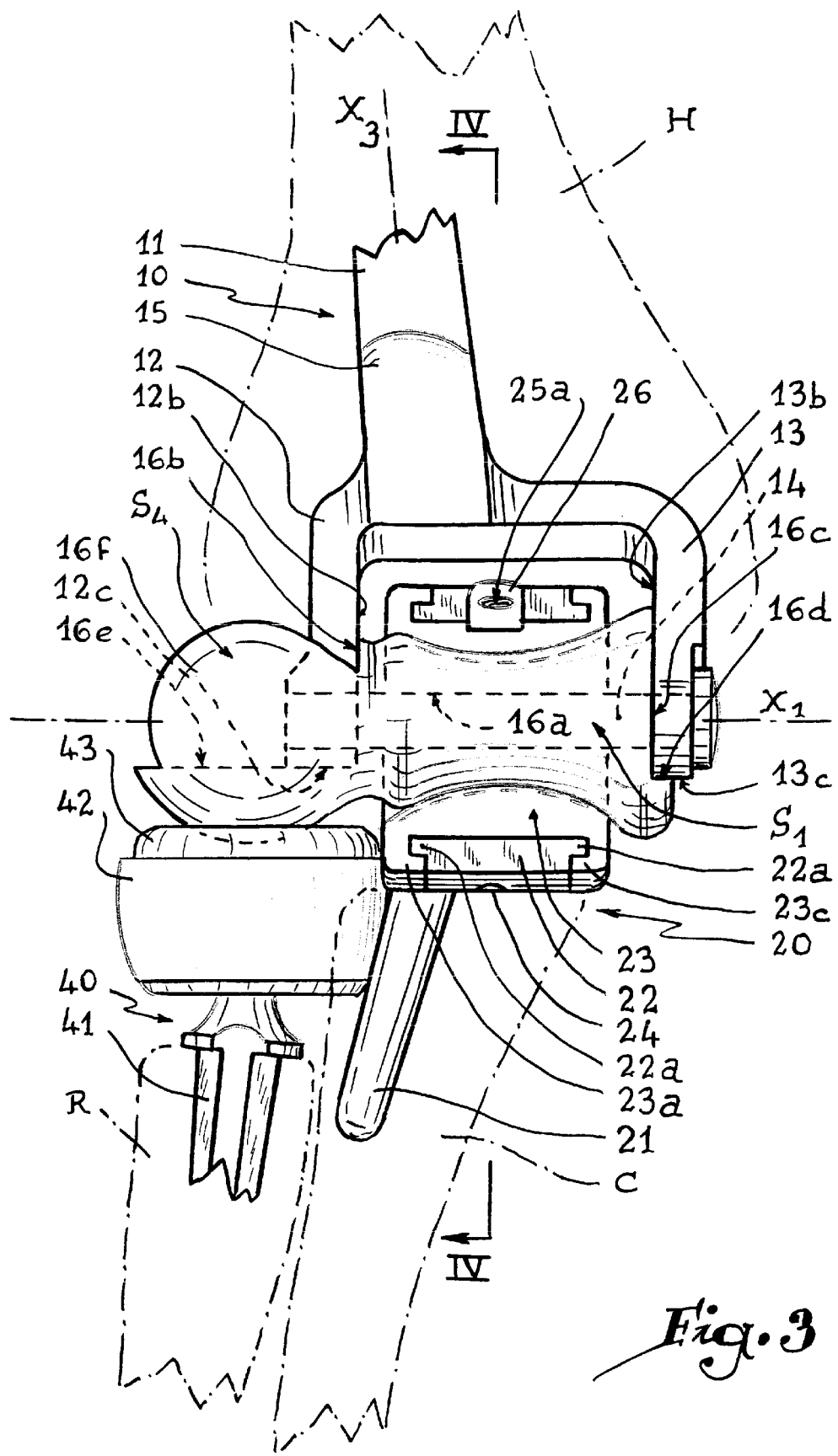
FIG. 3 is a front view of the prosthesis of FIG. 1 mounted in an elbow in extension, in a first configuration.
Figure 4:
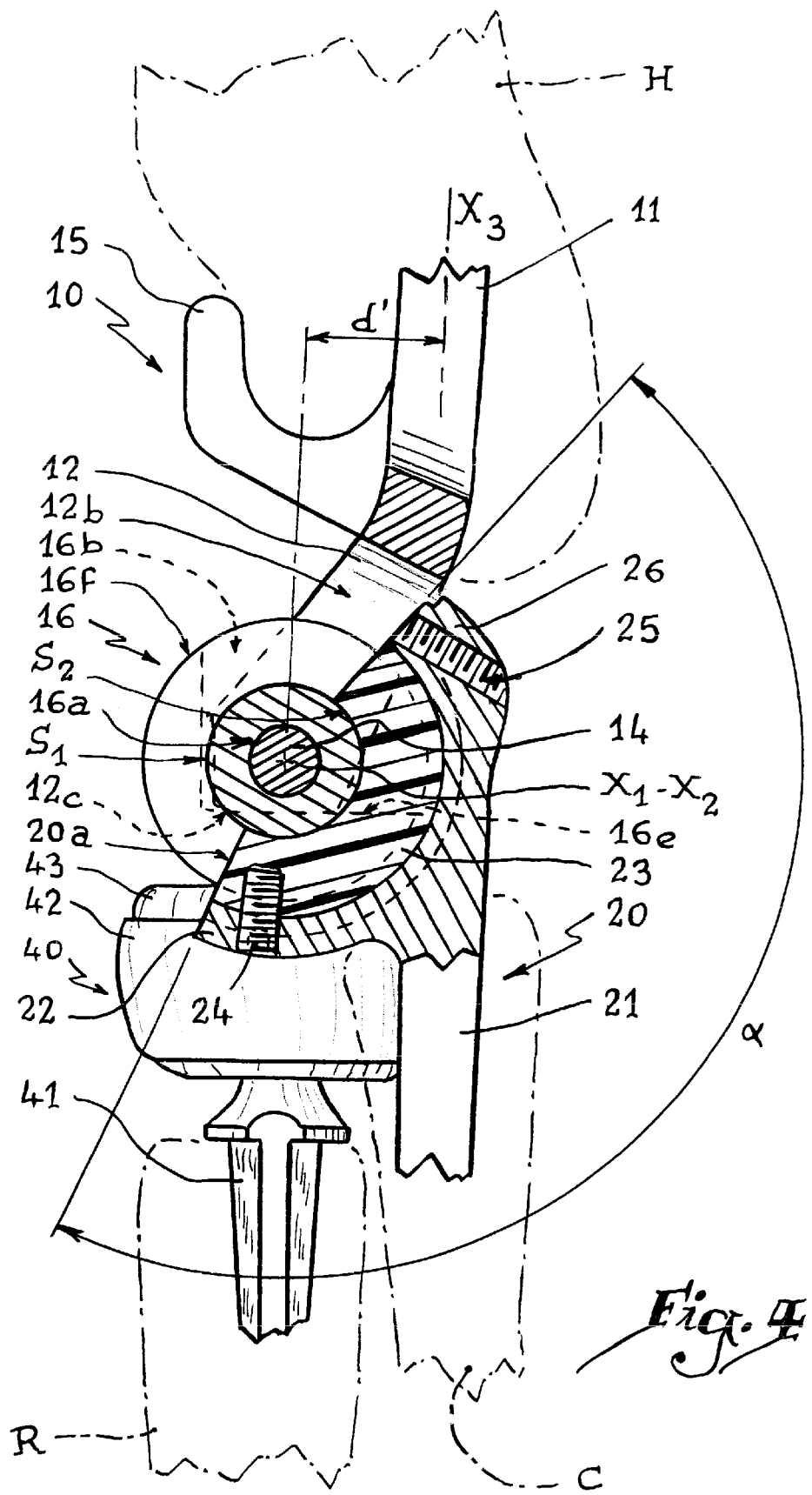
FIG. 4 is a section along plane IV—IV in FIG. 3.

The respective dimensions and orientations of the surfaces $S_1$ and $S_2$ are such that the ulnar component may be disposed around a part of the surface $S_1$, as shown in FIGS. 3 and 4. In this position, the lining 23 surrounds the piece 16 over a part of its circumference represented in FIG. 4 by an angle α defining the range of the congruence between the surfaces $S_1$ and $S_2$ visible in FIG. 4 and smaller than about 180°. The angle α is smaller than 180° in order to allow the positioning of the ulnar component on the piece 16. The operational clearances J and J' provided between the surfaces $S_1$ and $S_2$ can make it possible for the angle α to be greater than 180°, without compromising the free assembly of the component 20 on the piece 16.

In this configuration, the prosthesis behaves like a sliding prosthesis.

When the surgeon realizes that the tendons and ligaments of the joint are in good condition and that there is little risk of the joint being dislocated, the prosthesis can be used in the configuration of FIGS. 3 and 4.

Figure 6:
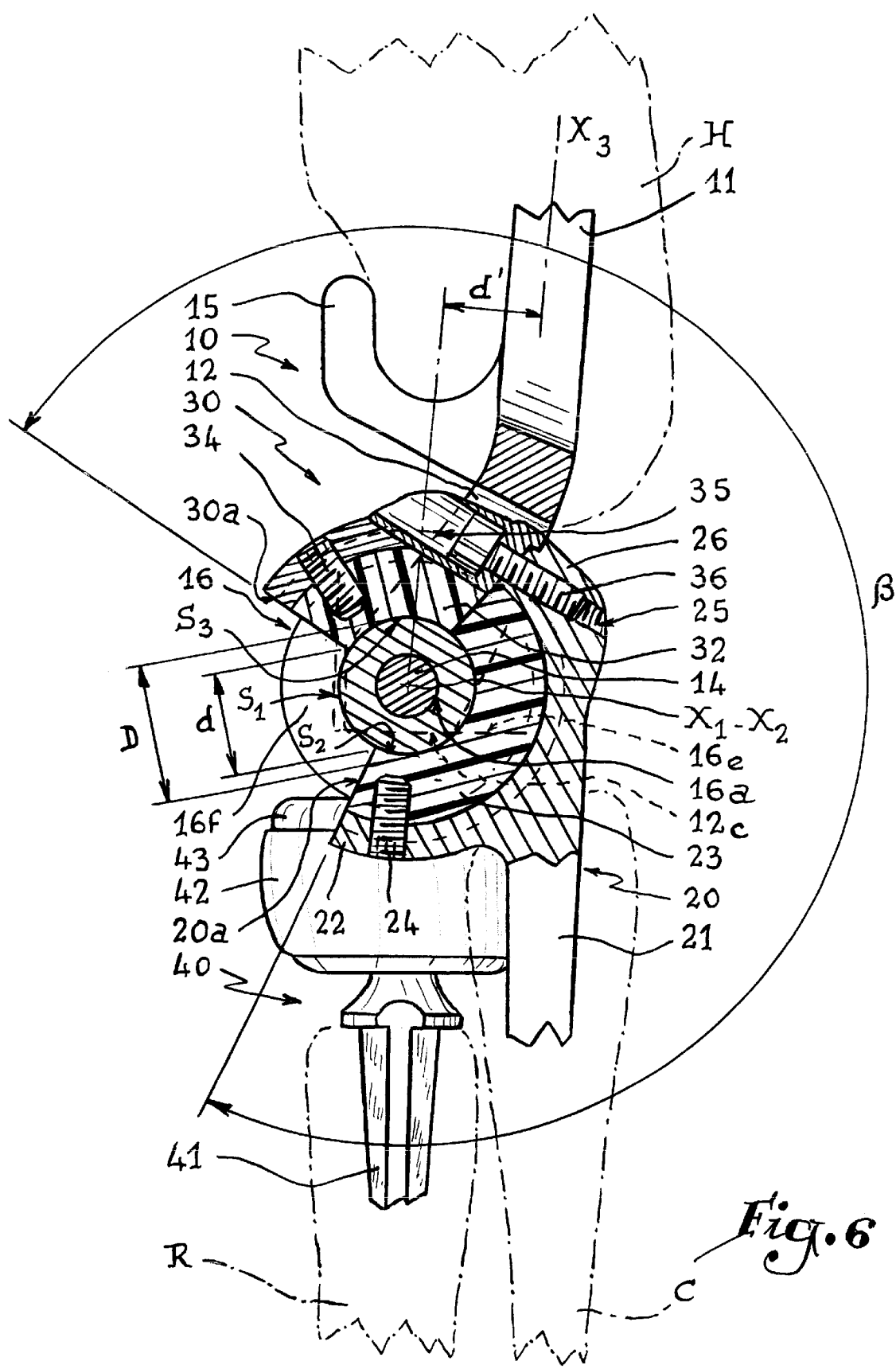
FIG. 6 is a section along plane VI—VI in FIG. 5.

According to the invention, the prosthetic joint can be rendered safer by using a locking element 30 intended to be mounted on the ulnar component 20 and formed by a reinforcement 32 and a lining 33 immobilized with respect to each other thanks to fins and returns similar to those of the tab 22 and the lining 23 and to a headless screw 34 visible in FIG. 6. The lining 33 is made of a material adapted for friction with the piece 16, for example polyethylene, this material advantageously being identical to that of the lining 23. The lining 33 is mounted on the reinforcement 32 in similar fashion to the assembly described with reference to FIG. 2.

A lateral notch 33b is provided on the lining 33, this notch being diametrally opposite the notch 23b when the element 30 is in mounted position and having the same function as the notch 23b.

The inner surface of the lining 33 forms a third articulating surface $S_3$ whose geometry is comparable to that of the surface $S_2$. More precisely, the generatrices of surfaces $S_2$ and $S_3$ are substantially identical, with the result that, when the element 30 is mounted on the component 20, the surface $S_3$ extends the surface $S_2$. The configuration is in that case that of FIGS. 5 and 6 in which the surfaces $S_2$ and $S_3$ of the assembly formed by the elements 20 and 30 surround the surface $S_1$, the axis $X_1$ and $X_2$ being able to be displaced with respect to each other, both in translation and in rotation, by distances or angles given by the value of the diametral and longitudinal functional clearances J and J' made between the surface $S_1$ and the combination of the surfaces $S_2$ and $S_3$. In effect, the combination of the surfaces $S_1$ and $S_2$ and $S_3$ make it possible to obtain:

- a sufficient contact surface between pieces 16 and 20 or 16, 20 and 30, whatever the relative position of the humeral and ulnar components.
- the possibility of a movement of varus-valgus and of an axial rotation whatever the efforts undergone by these components.
- the possibility of a medio-lateral translation of the ulna on the humerus.
- the possibility of an antero-posterior translation of the ulna on the humerus.

In the plane of FIG. 6, the surfaces $S_2$ and $S_3$ together surround the surface $S_1$ over an angle β of the order of 270°. In fact, the locking obtained thanks to the element 30 is efficient as long as angle β is greater than 180°. Satisfactory results have been obtained with an angle β included between 225 and 315°, this angle reasonably being able to extend over a range from 190 to 360°.

As long as the angle β is greater than 180°, the cooperation of surfaces $S_1$ on the one hand, $S_2$ and $S_3$ on the other hand, avoids a dislocation of the joint, while movements of varus-valgus remain possible by transverse slide and/or pivoting of the surfaces $S_2$ and $S_3$ with respect to the surface $S_1$.

Assembly of the element 30 on the component 20 is obtained thanks to a tapping 25 made in the boss 26 provided on the tab 22, while a housing 35 is provided in the reinforcement 32 for receiving a screw 36 intended to be tightened in the tapping 25. In an alternative solution, a tapping may be provided in the reinforcement 32 while a housing for receiving a screw head is provided in the tab 22. Other fixing means may be envisaged, in particular possibly truncated studs or a tenon-and-mortise assembly.

Figure 5:
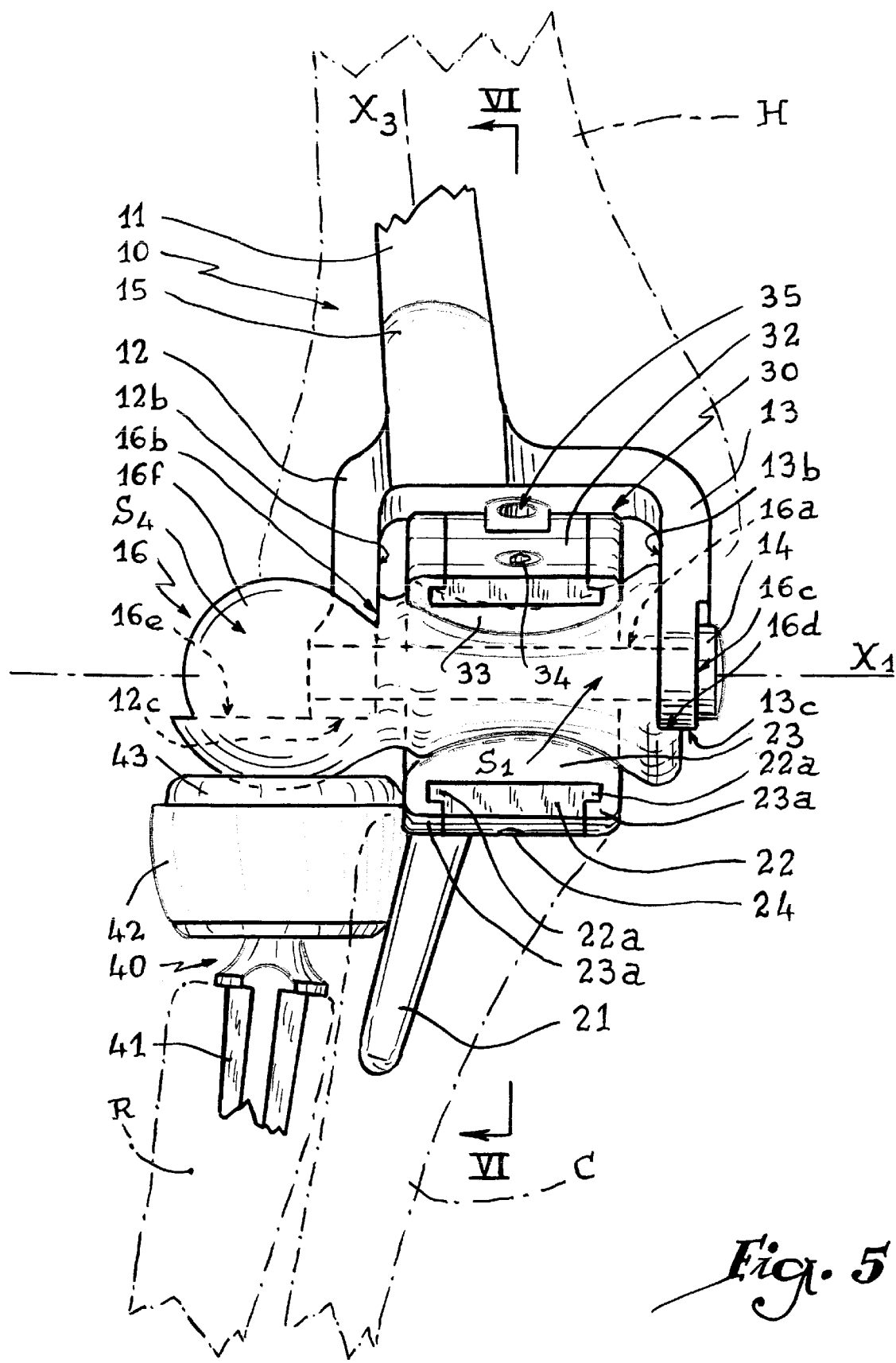
FIG. 5 is a view similar to FIG. 3 while the prosthesis is in a second configuration.

In the configuration of FIGS. 5 and 6, the distance d, between the respective free edges or ends 20a and 30a of the component 20 and of the element 30, is less than the minimum diameter D of the surface $S_1$, which corresponds to the desired locking thanks to the element 30.

$X_3$ denotes the longitudinal axis of the rod 11 and d' the shift of axes $X_1$ and $X_3$ in the plane of FIGS. 4 and 6. The value of d' is a parameter which depends on the patient's morphology.

According to an advantageous but non-compulsory aspect of the invention, it is possible to adjust the value of d' by using different pieces 16 whose central bore 16a is more or less offset with respect to axis $X_1$, as shown in dashed and dotted lines in FIG. 1 with references 16a' and 16a". In this way, after testing the rod 11 in the humerus, the surgeon can choose, from a plurality of pieces 16 of which the central bore is more or less offset with respect to the axis $X_1$, the one which best corresponds to the anatomical position of the trochlea.

In any case, the surfaces 12c and 13c of the tabs 12 come respectively into abutment against the surfaces 16d and 16e of the piece 16.

Other variants enable the same result to be obtained, in particular the use of pieces forming parts 11 to 15 of variable geometry, the orifices 12a and 13a being more or less offset with respect to axis $X_3$. In that case, a single elongated piece 16 may be used.

According to another alternative, elements 11 to 16 may be formed in one piece, an assembly forming a prosthesis comprising different one-piece assemblies of which the shift d' is variable. The surgeon may thus choose the most suitable piece from these one-piece assemblies, after having positioned and tested a temporary phantom prosthesis.

In practice, whatever the mode of adjustment of the shift envisaged, it appears that an amplitude of more or less 5 mm around the median position represented in solid lines in FIG. 1, covers the majority of the operational cases.

A radial component 40 is provided, comprising a rod 41 intended to be inserted in the medullar channel of the radius R and a head 43 made of plastics material, for example polyethylene encircled by a metallic hoop 42. The head 43 forms a concave articulating surface $S_5$ provided to come into abutment against the surface $S_4$ of the piece 16. In this configuration, the prosthesis of the invention is a total prosthesis.

According to a variant of the invention (not shown), the prosthesis may be partial, in that it does not comprise a radial component, the anatomical head of the radius in that case being directly articulated on the metallic surface $S_4$.

Figure 8:
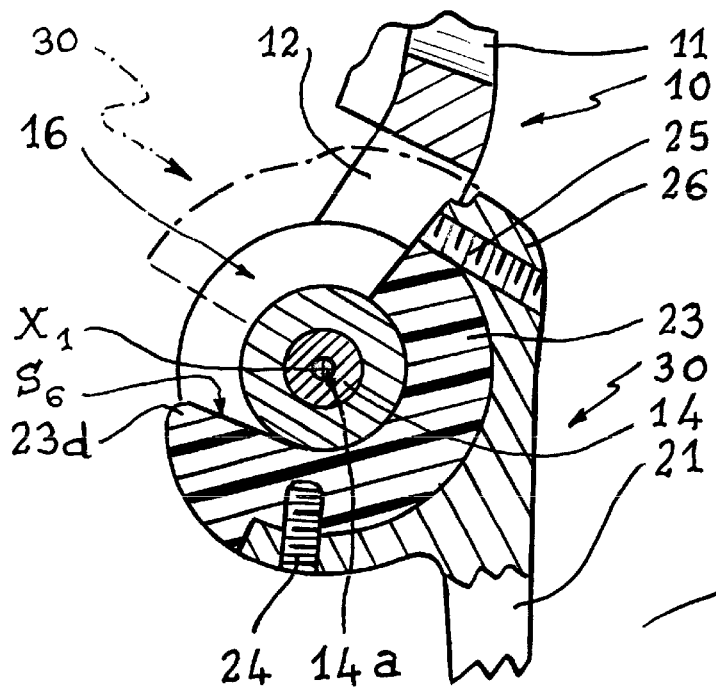
FIG. 8 is a partial section similar to FIG. 4 for a prosthesis in accordance with a second embodiment of the invention.

In the second embodiment of the invention shown in FIG. 8, element similar to those of the first embodiment hear identical references. A shoe 23d extends the lining 23 opposite its edge provided to come into contact with the element 30. The inner surface $S_6$ of the shoe 23d extends the surface $S_2$ tangentially, with the result that it constitutes an additional protection against a dislocation of the prosthesis, usable with or without the element 30 which may be mounted on the component 20 in the position shown in dashed and dotted lines. The locking obtained is further improved with respect to the first embodiment.

According to an advantageous but non-compulsory aspect of the invention, an axial orifice 14a is made longitudinally in the screw 14 so as to allow passage of suture threads intended to attach the ligamentary structures in contact with the prosthesis or the bone, near their anatomical point of anchoring located on the axis of bending of the elbow. An equivalent orifice may also he made in the piece 16, near the axis $X_1$ and parallel thereto, in particular in the one-piece variant mentioned hereinabove.

According to a variant of the invention applicable whatever the form of embodiment in question, the clearance between the surfaces $S_1$ and $S_2$ or between the surface $S_1$ and the combination of the surfaces $S_2$ and $S_3$ may be solely diametral or, on the contrary, not present any diametral clearance or present a very small diametral clearance, the operational clearance in that case being essentially longitudinal. In the first case, a good resistance to the movements of varus-valgus and of rotation is obtained, to the detriment of the transverse mobility. In the second case, operation is correct, but a certain wear of surfaces $S_1$, $S_2$ and $S_3$ can be expected.

What is claimed is:

1. An elbow prosthesis including a humeral component having a first, substantially cylindrical articulating surface, an ulnar component, said ulnar component including a concave tab member forming a second articulating surface adapted to be arranged around a portion of said first articulating surface so as to pivot about a longitudinal axis of said first articulating surface, said ulnar component including a locking element forming a third articulating surface, means for mounting said locking element to said concave tab member such that said third articulating surface forms an arcuate continuation of said second articulating surface adapted to be disposed around said first articulating surface, and said second and third articulating surfaces extending together in transverse section of said first articulating surface over more than 180° about said first articulating surface.

2. The prosthesis of claim 1, wherein said second and third articulating surfaces extend together over an angle included between 190° and 360° about said first articulating surface.

3. The prosthesis of claim 1, including means for adjusting a position of the longitudinal axis of said body member with respect to a longitudinal axis of a rod extending from said body member for anchoring said humeral component in a humerus of a patient.

4. The prosthesis of claim 3, wherein said body member is formed by an elongated piece having a bore, tabs extending from said rod are provided with an orifice, and pin means extendable through said orifices and said bore for securing said body member to said rod.

5. The prosthesis of claim 3, wherein said body member is formed in an elongated piece, means for securing said elongated piece to said rod, and said means for adjusting including a plurality of elongated pieces of differing structures such that by selection of a particular elongated piece makes it possible to obtain different positions of said longitudinal axis of said elongated pieces with respect to the longitudinal axis of said rod.

6. The prosthesis of claim 3, wherein said rod and body member are integrally formed, and said prosthesis including a plurality of such integrally formed body members and rods of different geometries.

7. The prosthesis of claim 7, wherein said concave tab members of said and said locking element of said ulnar component are each provided with a free end, the distance between said free ends being less than a minimum diameter of said first pivot surface when said locking element is mounted on said concave tab member.

8. The prosthesis of claim 1, wherein said means for mounting includes at least one tapping in one of said concave tab member and said locking element for receiving a screw engaged in a housing provided in the other of said concave tab member and said locking element.

9. The prosthesis of claim 1, wherein said first articulating surface presents a concave generatrix, and said second and third articulating surfaces present, in a plane of section parallel to the longitudinal axis of said first articulating surface, a convex generatrix.

10. The prosthesis of claim 1, wherein said body member includes a substantially convex articulating surface portion extending from said first articulating surface for engaging a radial component.

11. The prosthesis of claim 1, wherein a clearance is provided between said first articulating surface and said second and third articulating surfaces.

12. The prosthesis of claim 1, wherein said concave tab member and said locking element each includes a reinforcement and lining mounted on said reinforcement, and returns of each said lining cover lateral fins of said reinforcements.

13. The prosthesis of claim 1, wherein said body member includes an orifice for passage of at least one suture thread, said orifice being proximate said longitudinal axis of said first articulating surface and parallel thereto.

14. The prosthesis of claim 2 in which said second and third articulating surfaces extend over an angle of between 225 to 315° about said first articulating surface.

15. The prosthesis of claim 14 in which said second and third articulating surfaces extend at an angle of approximately 270° about said first articulating surface.

* * * * *

UNITED STATES PATENT AND TRADEMARK OFFICE
CERTIFICATE OF CORRECTION

PATENT NO. : 6,379,387 B1
DATED : April 30, 2002
INVENTOR(S) : Alain Tornier

It is certified that error appears in the above-identified patent and that said Letters Patent is hereby corrected as shown below:

<u>Column 7,</u>
Lines 38-56, should read:
     1. An elbow prosthesis including a humeral component including a body member having a first, substantially cylindrical articulating surface, an ulnar component, said ulnar component including a concave tab member forming a second articulating surface adapted to be arranged around a portion of said first articulating surface so as to pivot about a longitudinal axis of said first articulating surface, said ulnar component including a locking element forming a third articulating surface, means for mounting said locking element to said concave tab member such that said third articulating surface forms an arcuate continuation of said second articulating surface adapted to be disposed around said first articulating surface, and said second and third articulating surfaces extending together in transverse section of said first articulating surface over more than 180° about said first articulating surface.

UNITED STATES PATENT AND TRADEMARK OFFICE
CERTIFICATE OF CORRECTION

PATENT NO. : 6,379,387 B1
DATED : April 30, 2002
INVENTOR(S) : Alain Tornier

It is certified that error appears in the above-identified patent and that said Letters Patent is hereby corrected as shown below:

<u>Column 8,</u>
Lines 21-26, should read
    7.    The prosthesis of claim 1, wherein said concave tab member and said locking element of said ulnar component are each provided with a free end, the distance between said free ends being less than a minimum diameter of said first pivot surface when said locking element is mounted on said concave tab member.

Signed and Sealed this

Seventh Day of January, 2003

JAMES E. ROGAN
*Director of the United States Patent and Trademark Office*

UNITED STATES PATENT AND TRADEMARK OFFICE
Certificate

Patent No. 6,379,387 B1                                                                                          Patented: April 30, 2002

On petition requesting issuance of a certificate for correction of inventorship pursuant to 35 U.S.C. 256, it has been found that the above identified patent, through error and without any deceptive intent, improperly sets forth the inventorship.
    Accordingly, it is hereby certified that the correct inventorship of this patent is: Alain Tornier, St. Ismier (FR); Shawn O'Driscoll, Rochester, MN (US); Graham King, London, Ontario (CA); Ken Yamaguchi, St. Louis, MO (US); Yves Alain Ratron, Grenoble (FR); and Bruno Scialom, Gieres (FR).

Signed and Sealed this Fifteenth Day of November 2011.

THOMAS J. SWEET
                                                                          *Supervisory Patent Examiner*
                                                                                                     Art Unit 3738
                                                                           Technology Center 3700